United States Patent
Burns et al.

(10) Patent No.: US 6,941,806 B2
(45) Date of Patent: Sep. 13, 2005

(54) METHOD, APPARATUS AND SYSTEM FOR SENSING AIR BORNE HAZARDOUS MATERIALS

(75) Inventors: Joseph D Burns, Franktown, CO (US); Mark V Anderson, Evergreen, CO (US)

(73) Assignee: AirDat, LLC, Evergreen, CO (US)

( * ) Notice: Subject to any disclaimer, the term of this patent is extended or adjusted under 35 U.S.C. 154(b) by 75 days.

(21) Appl. No.: 10/696,377

(22) Filed: Oct. 29, 2003

(65) Prior Publication Data

US 2004/0189976 A1 Sep. 30, 2004

Related U.S. Application Data

(60) Provisional application No. 60/422,790, filed on Oct. 31, 2002.

(51) Int. Cl.[7] .................................................. G01W 1/00
(52) U.S. Cl. ................................ 73/170.02; 73/170.01; 73/170.07
(58) Field of Search ........................... 73/170.01–170.15

(56) References Cited

U.S. PATENT DOCUMENTS

| | | | |
|---|---|---|---|
| 3,751,984 A | | 8/1973 | Rennie |
| 3,768,302 A | | 10/1973 | Barringer |
| 3,970,428 A | | 7/1976 | Barringer |
| 4,654,528 A | | 3/1987 | Cloud, Jr. et al. |
| 5,311,194 A | * | 5/1994 | Brown .................. 342/357.06 |
| 5,347,285 A | * | 9/1994 | MacDoran et al. .... 342/357.12 |
| 5,652,717 A | | 7/1997 | Miller et al. |
| 5,742,053 A | * | 4/1998 | Rekunyk .................. 250/338.5 |
| 5,808,916 A | | 9/1998 | Orr et al. |
| 5,815,417 A | | 9/1998 | Orr et al. |
| 5,831,876 A | | 11/1998 | Orr et al. |
| 6,008,928 A | | 12/1999 | Sashse et al. |
| 6,281,970 B1 | | 8/2001 | Williams et al. |
| 6,317,080 B1 | | 11/2001 | Baxter, Jr. |
| 6,425,286 B1 | | 7/2002 | Anderson et al. |
| 6,430,996 B1 | | 8/2002 | Anderson et al. |
| 6,553,336 B1 | | 4/2003 | Johnston et al. |
| 2002/0188522 A1 | | 12/2002 | McCall et al. |
| 2003/0069002 A1 | | 4/2003 | Hunter et al. |

* cited by examiner

*Primary Examiner*—Edward Lefkowitz
*Assistant Examiner*—Jermaine Jenkins
(74) *Attorney, Agent, or Firm*—Ancel W. Lewis, Jr.

(57) ABSTRACT

Apparatus for detecting hazardous materials is mounted on an aircraft and has a sensor, a heading unit, a transceiver and a GPS unit. The sensor has an airfoil shaped probe and an electronics module. The probe has a positive airflow, enclosed sensing chamber with a hazardous material sensing element. The system for detecting hazardous materials includes aircraft with the hazardous material detecting apparatus and a ground network. The method for detecting hazardous materials includes the steps of providing aircraft with hazardous material sensing apparatus and a ground network, collecting hazardous material and atmospheric data with the sensing apparatus, transmitting the position, wind velocity and hazardous material data to the ground network, calculating distribution of hazardous materials in the atmosphere, generating a real-time map of distribution of hazardous materials and predicting dispersion of the hazardous materials in the atmosphere.

17 Claims, 2 Drawing Sheets

METHOD, APPARATUS AND SYSTEM FOR SENSING AIR BORNE HAZARDOUS MATERIALS

This application claims the benefit under 35 U.S.C. § 119(e) of the U.S. provisional patent application No. 60/422,790 filed Oct. 31, 2002.

TECHNICAL FIELD

The present invention relates to chemical, biological, radioactivity and air pollutant detectors and more particularly to a method, apparatus and system for rapidly measuring the presence, distribution, and dispersion of hazardous materials in the atmosphere.

BACKGROUND ART

Prior known sensors and systems used for sensing hazardous agents include hand-held gas chromatography "sniffing" devices, spectral analyzers, biological testing cultures, live animal exposures, and Geiger counters. Hand-held gas chromatography, spectral analyzers, and Geiger counters are intended for spot measurement and are generally cumbersome, bulky, and traditionally complex and hard to rapidly deploy. Additionally, they are not intended for continual measurements except in a localized area. They also are typically stand-alone and do not incorporate other environmental conditions into their readings.

Biological testing using cultures does not provide immediate results. Generally, hazardous agent testing is limited to a single measurement and requires the tester to maintain a physical proximity to the potential hazard. Hazardous agent testing is typically practical to test in a small suspected contamination area.

Geiger counters and other radioactivity detection means do not provide assessment of the distribution of hazardous agents throughout the atmosphere at a range of altitudes and geographic locations.

All of the approaches above involve exposing the hazardous sensing element to the immediate environment to sense for a known contaminant at a fixed, single location. These approaches also require suspicion that such a potential threat exists. In each measurement approach difficulties and inaccuracies are introduced into the determination of a potential hazard by manual handling of the test. Additionally, other atmospheric factors such as winds aloft and convective activity that could potentially influence the spread of such a contaminant are not integrated into any of the above mentioned testing outputs. As such, the sensing and predicted path of a potential hazardous agent is not possible or is very difficult and limited under current approaches. Present methods of hazardous agent detection do not provide assessment of the distribution and dispersion of hazardous agents throughout the atmosphere at a range of altitudes and geographic locations.

The need exists for a method to rapidly measure the presence, distribution, and dispersion of hazardous agents in the atmosphere. Hazardous agents include biological, chemical, or radioactive agents resulting from accidents and terrorism incidents, and air pollution resulting from normal economic activities. A sensor for detecting hazardous agents and measuring specific air parameters in any airflow environment would be useful. An integrated sensing system suitable for aircraft mounted hazardous agent detection, combined with measurements of ambient atmospheric conditions, would be particularly useful. The sensing system would detect hazardous agents and provide the atmospheric information necessary to assess how those agents would be distributed and dispersed in the atmosphere due to winds, turbulence, and convective activity.

Prior known aircraft mounted probes for ice detection and air data collection are disclosed in U.S. Pat Nos. 6,430,996 and 6,425,286 to Anderson et al., incorporated herein by reference.

DISCLOSURE OF THE INVENTION

A system for measuring hazardous materials in the atmosphere includes one or more aircraft mounted hazardous material sensing apparatus in communication with a ground network. The hazardous material sensing apparatus has a transceiver for communication with the ground network, a Global Positioning System (GPS) unit for providing location and time of observation data, and a sensor. The sensor includes a probe protruding into the airflow and an electronics module for measuring hazardous materials and atmospheric parameters. The sensor has temperature, pressure and humidity sensors as well as sensors for hazardous materials. The method of sensing hazardous materials in the atmosphere includes the steps of providing aircraft with hazardous material sensing apparatus and a ground network, collecting hazardous material and atmospheric data with the sensing apparatus, transmitting the data to the ground network, calculating distribution of hazardous materials in the atmosphere, generating a real-time map of distribution of hazardous materials and predicting dispersion of the hazardous materials in the atmosphere.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
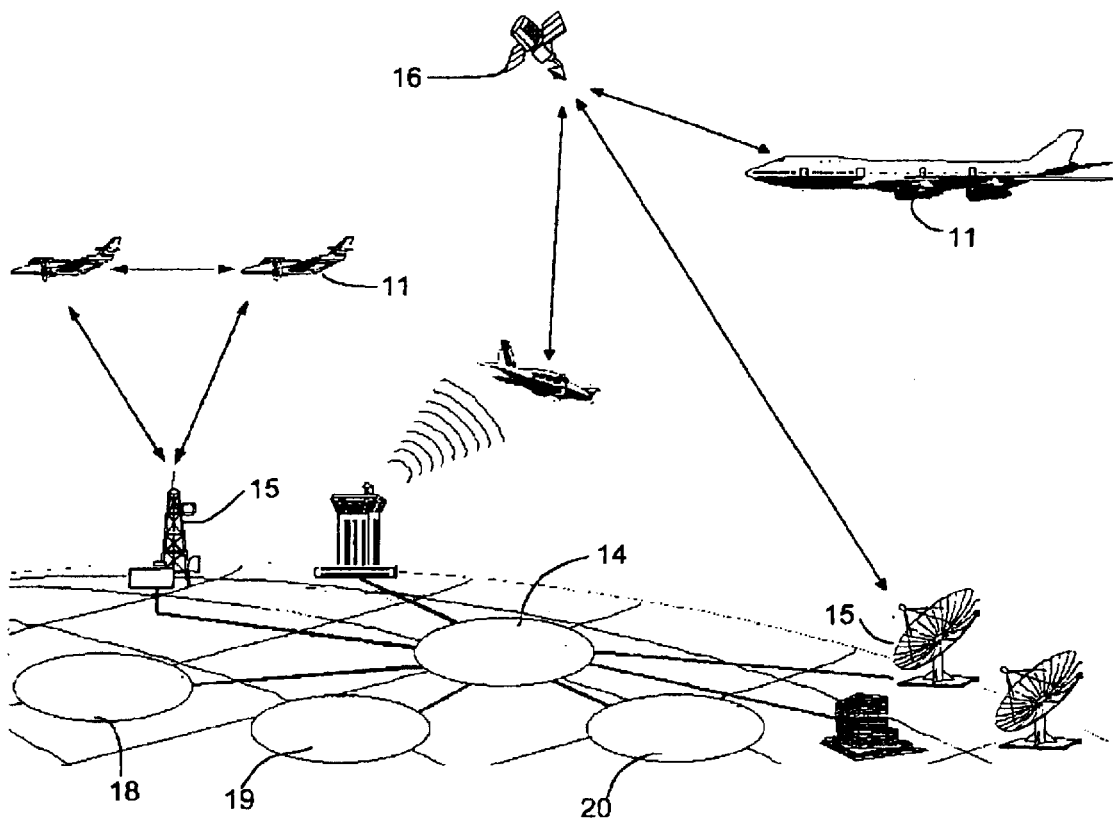
FIG. 1 is an illustrative view of a system embodying features of the present invention.
Figure 2:
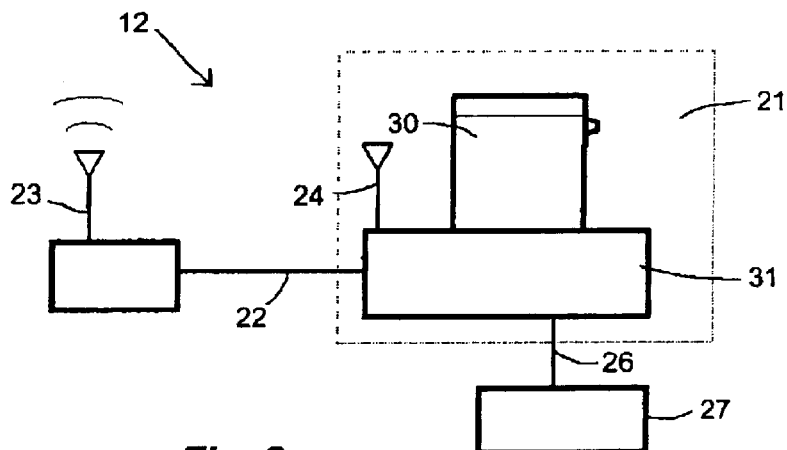
FIG. 2 is a diagramic view of a sensing apparatus of the system of FIG. 1.

Referring now to FIGS. 1 and 2, a system embodying features of the present invention includes aircraft 11 equipped with hazardous material sensing apparatus 12, and a ground network 14. The ground network 14 includes communications towers 15, for receiving data from the sensing apparatus 12, linked to computers that store and analyze the data. Preferably the aircraft 11 and ground network 14 are linked through communications satellites 16. The ground network 14 may further include links to government agencies such as the National Weather Service 18, the NOAA/Meteorological Modeling Labs 19 or a DOD Analysis Facility 20.

The sensing apparatus 12, as shown in FIG. 2 has a GPS unit 24 and a sensor 21, linked by a first data line 22 to a transceiver 23 and by a second data line 26 to a heading module 27. The sensor 21 provides an ASCII or binary output via the first data line 22 directly to the transceiver. The GPS unit 24 provides time, position and altitude tagging of the detection events and observations. Atmospheric and hazardous material data from the sensor 21, and position and altitude data from the GPS unit 24 are transmitted by the transceiver 23 to the towers 15 of the ground network 14. The heading module 27 enables calculation of wind velocity. Multiple sets of atmospheric data may be buffered and transmitted together to minimize transmission costs.

Figure 3:
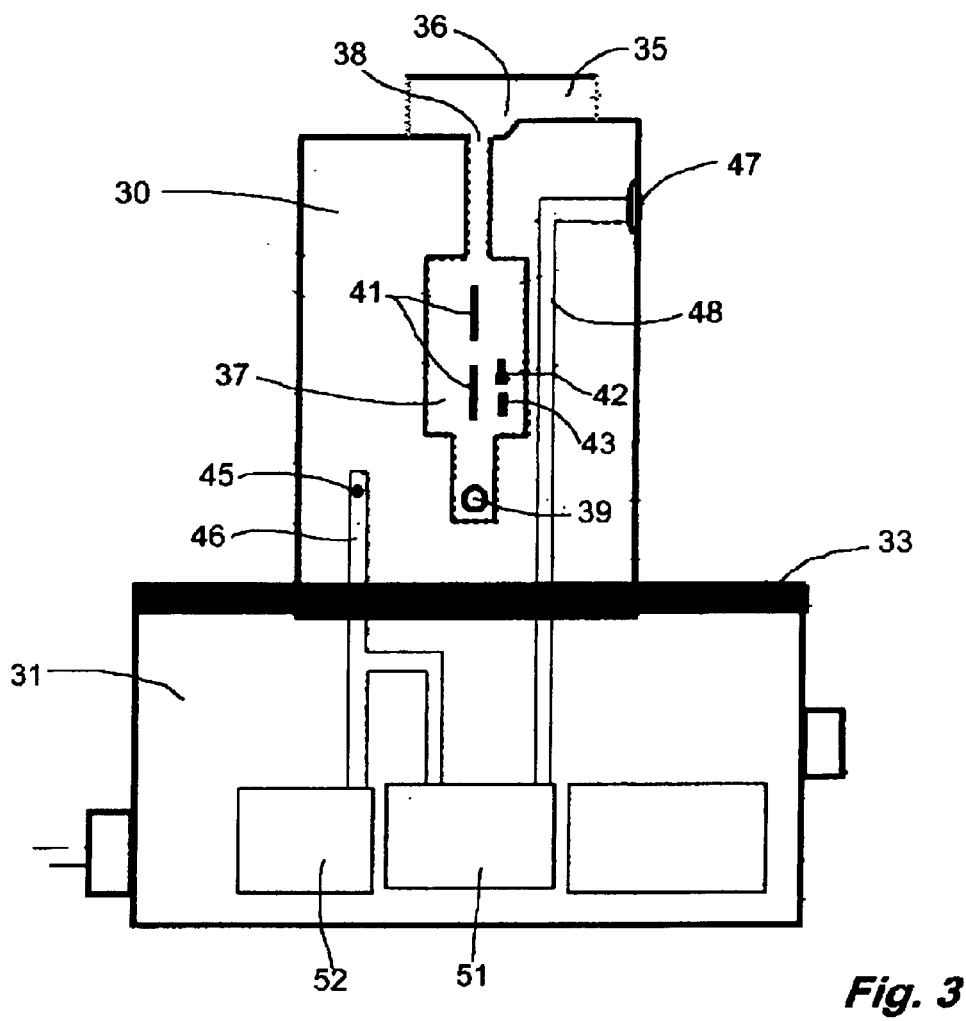
FIG. 3 is a side diagramic view of the sensor of the apparatus of FIG. 2.
Figure 4:
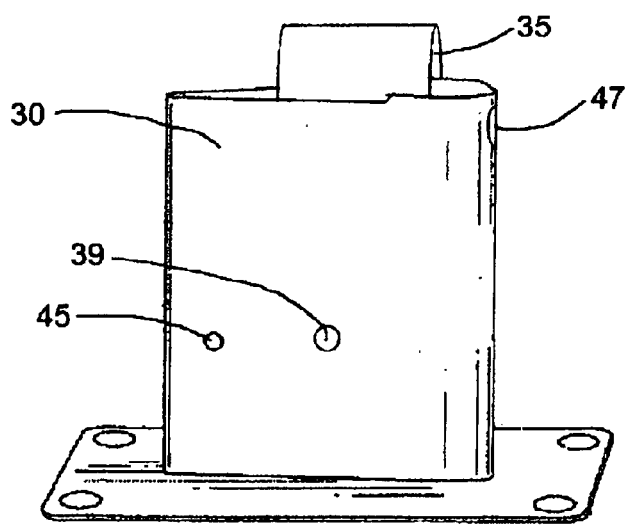
FIG. 4 is a perspective view of the probe of the apparatus of FIG. 2.

Referring to FIGS. 3 and 4, the sensor 21 has a probe 30 and an electronics module 31. The probe 30 is airfoil shaped for minimum drag and protrudes outside of the aircraft skin 33 into the airflow. The electronics module 31 is located under the skin of the aircraft. The probe 30 includes a top mounted flow tube 35 that opens in the direction of the airflow over the aircraft 11. The flow tube 35 has a diverging portion 36, so that the cross-sectional area and pressure in the flow tube are greater downstream from the diverging portion 36 than upstream from the diverging portion 36.

An enclosed sensing chamber 37 connects to the flow tube 35 through an inlet hole 38 in the flow tube 35 downstream from the diverging portion 36. The sensing chamber 37 extends downwardly from the inlet hole 38. A transversely opening outlet hole 39 connects near the bottom of the sensing chamber 37. The pressure is greater at the inlet hole 38 than at the side opening outlet hole 39, assuring positive air flow through the sensing chamber 37, and providing a continuous sampling of the outside air. The geometry of the top of the probe 30 and flow tube 35 minimizes water and contaminant entry into the sensing chamber 37.

Hazardous sensing elements 41 are located in the positive flow-through sensing chamber 37. Preferably the hazardous sensing elements 41 are "chip-based" hazardous agent sensors, such as pin diode radiation detectors, and biohazard and chemical detection IC's, that report back either a yes/no digital or analog sensing signal. Such "chip-based" hazardous agent sensors allow for sensing of specific hazardous threats and harmful agents, and can quickly be field replaced by opening up the sensing chamber and plugging in the respective appropriate chip/PCB board combination in order to detect other agents. A temperature sensor 42 inside the sensing chamber 37 measures total temperature. A humidity sensor 43 is located in the sensing chamber 37. A heater can also be incorporated into the probe 30 for de-icing purposes.

Two spaced interconnected static ports 45 open on opposite sides of the probe 30 and connect to a downwardly extending static tube 46. A forwardly opening pitot tube opening 47 connects to a rearwardly, then downwardly extending pitot tube 48. The electronics module 31 includes a differential pressure sensor 51, connected to the static tube 46 and the pitot tube 48, for measuring airspeed, and a static pressure sensor 52 connected to the static tube 46 for measuring ambient pressure.

In the illustrated embodiment, the GPS unit 24 is integrated into the electronics module 31. Alternatively, a combined transceiver/GPS unit may be provided or the GPS unit 24 may be a stand alone unit. The hazardous sensing elements 41, the temperature sensor 42 and the humidity sensor 43 connect to the electronics module 31. The temperature sensor 42 measures total temperature and corrections for mach heating are incorporated into the microprocessor in the electronics module 31 to determine ambient temperature. The signals from the hazardous sensing elements 41 are fed, as required, into an analog to digital converter and processed with the other environmental conditions. Wind velocity (speed and direction) is the difference between air velocity and actual velocity, and is calculated from the air speed from the differential pressure sensor 51, heading from the heading module 27 and actual velocity from the GPS unit 24. The resultant data can then be stored or immediately downlinked to the ground network 14.

A method of sensing hazardous materials in the atmosphere includes the steps of providing aircraft 11 with hazardous material sensing apparatus 12 and a ground network 14, collecting hazardous material and atmospheric data with the sensing apparatus 12, transmitting the data to the ground network 14, calculating distribution of hazardous materials in the atmosphere from the data, generating a real-time map of distribution of hazardous materials and predicting dispersion of the hazardous materials in the atmosphere. The present invention provides continuous, automated sampling of the environment with a positive airflow over a hazardous sensing element 41 while permitting protection of the hazardous sensing element 41 from that environment. Deploying the sensing apparatus 12 on a variety of aircraft 11 and other modes of moving transportation allows generation of a real-time map of any potential threat or distribution of hazardous agents, along with dispersement projections. One may extrapolate potential threat or risk level from knowledge of the current environmental conditions in combination with the output signal from hazardous sensing elements 41.

The data received from the sensing apparatus 12 is processed in near real time to create a map of the location and level of the hazard, along with atmospheric conditions such as temperature, humidity, wind velocities aloft, and atmospheric turbulence. Such a map will be an invaluable tool for agencies in the tracking of any potential airborne hazards. Additional embodiments can be modified for tracking of other airborne particulates and contaminates, including pollutants. Combining the sensor 21 with a low cost transceiver 23, and existing communications infrastructures provides a unique opportunity to significantly improve airborne, continuous surveillance of potential biological, chemical, radioactive, and pollutant hazards in an inexpensive, mass deployable package. The present invention overcomes the problems of earlier hazardous agent sensing technologies by measuring the hazardous or harmful agent along with the temperature, pressure, humidity, and wind velocities within a single aircraft mounted sensor 21 utilizing a positive airflow sensing chamber 37.

Although the present invention has been described with a certain degree of particularity, it is understood that the present disclosure has been made by way of example and that changes in details of structure may be made without departing from the spirit thereof.

What is claimed is:

1. Apparatus, for mounting on an aircraft, for detecting hazardous materials, comprising:
   a global positioning system unit,
   a heading module, and
   a sensor having a probe, an electronics module, and means for measuring airspeed, said probe being mounted to protrude outside the skin of said aircraft, and including an enclosed, positive airflow, sensing chamber with a sensing element for a selected hazardous material mounted therein, said electronics module being connected to and configured to receive input from said global positioning system unit, said heading module, said sensing element and said means for measuring airspeed, said electronics module being configured to output data including position, altitude, wind velocity and hazardous material detection information,
   whereby distribution of said selected hazardous material may be mapped and dispersion of said selected hazardous material may be predicted.

2. Apparatus as set forth in claim 1 including a transceiver connected to said electronics module for transmitting said data to a ground network.

3. Apparatus as set forth in claim 2 wherein said global positioning system unit and said electronics module are a combined unit.

4. Apparatus as set forth in claim 1 wherein said probe has an airfoil shape, and includes an outwardly located flow tube opening in the direction of airflow with said chamber being connected to and extending inwardly from said flow tube, and an inwardly located outlet hole connected to said chamber opposite said flow tube and opening transverse to the direction of airflow.

5. Apparatus as set forth in claim 4 wherein said means for measuring airspeed includes a forwardly opening pitot tube and pair of spaced, side opening static ports, in said probe, all connected to a differential pressure sensor in said electronics module.

6. Apparatus as set forth in claim 5 wherein said static ports are connected to a static pressure sensor in said electronics module.

7. Apparatus as set forth in claim 1 wherein said probe includes a temperature sensor and a humidity sensor, each located in said chamber and connected to said electronics module.

8. Apparatus as set forth in claim 1 wherein said sensing element is a plug-in, chip based hazardous agent sensor.

9. Apparatus, for mounting on an aircraft, for detecting hazardous materials, comprising:
   a global positioning system unit,
   a heading module,
   a sensor having an airfoil shaped probe mounted to protrude outside the skin of said aircraft, and an electronics module, said probe having an outwardly located flow tube opening in the direction of airflow, an inwardly extending, enclosed, positive airflow, sensing chamber connected to said flow tube and at least one inwardly located outlet hole connected to said chamber opposite said flow tube, opening transverse to the direction of airflow, a forwardly opening pitot tube, and pair of spaced, side opening static ports, said chamber having a plug-in, chip based sensing element for a selected hazardous material, a temperature sensor and a humidity sensor mounted therein, said electronic module having a static pressure sensor connected to said static ports and a differential pressure sensor connected to said pitot tube and said static ports, said electronics module being connected to and configured to receive input from said global positioning system unit, said heading module, said sensing element, said temperature sensor, and said humidity sensor, said electronics module being configured to output data including position, altitude, wind velocity, temperature, humidity and hazardous material detection information, and
   a transceiver connected to said electronics module for transmitting said data to a ground network,
   whereby distribution of said selected hazardous material may be mapped and dispersion of said selected hazardous material may be predicted.

10. A method of predicting hazardous material dispersion comprising the steps of:
   providing aircraft with hazardous material sensing apparatus for sensing position, altitude, wind velocity and a hazardous material mounted thereon,
   collecting position, altitude, wind velocity and hazardous material data with said sensing apparatus while said aircraft flies, and
   mapping distribution of said hazardous material and wind velocity from said data to predict dispersion of said hazardous material.

11. The method as set forth in claim 10 including the steps of
   providing a ground network, and
   transmitting said data from said aircraft to said ground network for said step of mapping.

12. The method as set forth in claim 10 wherein said step of mapping includes receiving weather forecast information from a weather forecast service and combining said forecast information with said data.

13. The method as set forth in claim 10 wherein said sensing apparatus includes a global positioning system unit, a heading module and a sensor connected to said global positioning system unit and said heading module, said sensor having an airfoil shaped probe mounted to protrude outside the skin of said aircraft and an electronics module, said probe including an enclosed, positive airflow, sensing chamber with a sensing element for said hazardous material mounted therein.

14. A method of predicting hazardous material dispersion comprising the steps of:
   providing aircraft with hazardous material sensing apparatus for sensing position, altitude, wind velocity and a hazardous material mounted thereon, including a global positioning system unit, a heading module and a sensor connected to said global positioning system unit and said heading module, said sensor having an airfoil shaped probe mounted to protrude outside the skin of said aircraft and an electronics module, said probe including an enclosed, positive airflow, sensing chamber with a sensing element for said hazardous material mounted therein,
   collecting position, altitude, wind velocity and hazardous material data with said sensing apparatus while said aircraft flies,
   providing a ground network,
   transmitting said data from said aircraft to said ground network,
   receiving weather forecast information from a weather forecast service,
   combining said forecast information with said data, and
   mapping distribution of said hazardous material and wind velocity from said forecast information and said data to predict dispersion of said hazardous material.

15. A system for detecting and mapping distribution of a hazardous material comprising:
   aircraft mounted sensing apparatus configured to collect position, altitude, wind velocity and hazardous material data, and including a global positioning system unit, a heading module, a transceiver and a sensor having a probe and an electronics module, said probe being mounted to protrude outside the skin of said aircraft, and including an enclosed, positive airflow, sensing chamber with a sensing element for said hazardous material mounted therein and pressure, temperature and humidity sensors, said electronics module being connected to and configured to receive input from said global positioning system unit, said heading module, and said probe, and to output said data, said transceiver being configured to transmit said data, and a ground network configured to receive said data and, from said data, to map distribution and predicted dispersion of said hazardous material.

16. The system as set forth in claim 15 wherein said probe has an airfoil shape, and includes an outwardly located flow tube opening in the direction of airflow with said chamber being connected to and extending inwardly from said flow tube, and at least one inwardly located outlet hole connected to said chamber opposite said flow tube and opening transverse to the direction of airflow.

17. The method as set forth in claim 15 wherein said sensing element is a plug-in, chip based hazardous agent sensor.

* * * * *